United States Patent
Zanini et al.

(10) Patent No.: US 6,891,055 B2
(45) Date of Patent: May 10, 2005

(54) PROCESS FOR THE PRODUCTION OF BIS (TRIMETHYLSILYLOXY) SILYLALKYLGLYCEROL METHACRYLATES

(76) Inventors: Diana Zanini, 3652 Fallon Oaks Dr., Jacksonville, FL (US) 32277; Frank Molock, 1543 Wild Fem Dr., Orange Park, FL (US) 32003

(*) Notice: Subject to any disclaimer, the term of this patent is extended or adjusted under 35 U.S.C. 154(b) by 0 days.

(21) Appl. No.: 10/610,271

(22) Filed: Jun. 30, 2003

(65) Prior Publication Data

US 2004/0267039 A1 Dec. 30, 2004

(51) Int. Cl.$^7$ .............................. C07F 7/08; C07F 7/20
(52) U.S. Cl. ...................... 556/436; 437/449; 437/450; 437/453; 437/456; 437/465; 437/466; 560/205; 560/218
(58) Field of Search ................................ 556/436, 437, 556/449, 450, 453, 456, 465, 46; 560/205, 218

(56) References Cited

U.S. PATENT DOCUMENTS 6,380,424 B1 * 4/2002 Yoneda et al. .............. 560/209
6,414,182 B1 * 7/2002 Shingai et al. .............. 560/209

FOREIGN PATENT DOCUMENTS

WO WO 2004014837 A1 * 2/2004 ........... C07C/67/26

* cited by examiner

*Primary Examiner*—Randy Gulakowski
*Assistant Examiner*—Marc S. Zimmer

(57) ABSTRACT

The present invention relates to a process for producing substituted glycerol acrylates from substituted epoxides. More specifically, the present invention relates to a process comprising the steps of (a) reacting a first reaction mixture comprising substituted epoxide with at least one epoxide opening catalyst and at least one acrylic acid to form a first reaction product comprising between about 60 and about 85 mole % substituted glycerol acrylate and said substituted epoxide;

(b) treating said first reaction mixture with a nucleophilic compound to form a second reaction product which is substantially free of said substituted epoxide and which comprises said substituted glycerol acrylate and a nucleophile derivative of said substituted epoxide; and (c) treating said second reaction product to remove said nucleophile derivative and produce substituted glycerol acrylate having less than about 5 weight % difunctional impurities.

24 Claims, No Drawings

PROCESS FOR THE PRODUCTION OF BIS (TRIMETHYLSILYLOXY) SILYLALKYLGLYCEROL METHACRYLATES

FIELD OF THE INVENTION

The present invention relates to processes for the production of silcone monomers and particularly bis (trimethylsilyloxy)silylalkyl glycerol methacrylates.

BACKGROUND OF THE INVENTION

Various silicone containing monomers have found utility as starting materials in the production of medical devices, such as ophthalmic devices and particularly, soft contact lenses having improved permeability to oxygen. One class of suitable monomers includes tris and bis (trimethylsilyloxy)silylalkyl glycerol methacrylates ("SiAGMA"). One process for making SiAGMA includes reacting the epoxide of the SiAGMA with methacrylic acid and either the sodium, potassium or lithium salt of methacrylic acid and an inhibitor, such as hydroquinone monomethyl ether. Reaction conditions include heating for about 15 hours, and yields SiAGMA having a purity of between about 75 to 95% and a number of byproducts, including dimethacrylated byproducts. When included in the monomer mixes used to make ophthalmic devices such as contact lenses, the dimethacrylated byproducts can act as crosslinkers, which even in small quantities can change the modulus of the resulting device. Accordingly, the concentration of these difunctional byproducts must either be tightly controlled or minimized. Removal of the difunctional byproducts is conventionally done by a cumbersome silica gel column chromatography step.

Thus, there remains in the art, a need for an improved process for the production of SiAGMA type compounds, and particularly one which minimizes the formation of difunctional byproducts.

SUMMARY OF THE INVENTION

The present invention relates to a process comprising the steps of (a) reacting a first reaction mixture comprising substituted epoxide with at least one epoxide opening catalyst and at least one acrylic acid to form a first reaction product comprising between about 60 and about 85 mole % substituted glycerol acrylate and said substituted epoxide;

(b) treating said first reaction mixture with a nucleophilic compound to form a second reaction product which is substantially free of said substituted epoxide and which comprises said substituted glycerol acrylate and a nucleophile derivative of said substituted epoxide; and (c) treating said second reaction product to remove said nucleophile derivative and produce substituted glycerol acrylate having less than about 5 weight % difunctional impurities.

DESCRIPTION OF THE INVENTION

Suitable substituted epoxides include those of Formula I below:

Wherein $R^1$ is any substituent which would not react with a nucleophilic compound.

Preferred epoxides include those shown in Formula II, below:

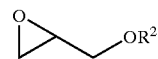

Wherein $R^2$ is a C1 to C12 alkyl substituted with at least one Si containing moiety and preferably at least one silicone. Suitable Si containing compounds include compounds of the formula III:

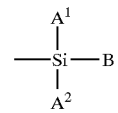

wherein $A^1$ and $A^2$ are the same or different and are selected from lower alkyl and B and; and B is a group of the structure:

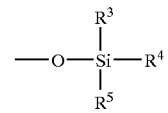

wherein $R^3$, $R^4$ and $R^5$ are the same or different and are selected from the group including lower alkyl, phenyl, benzyl, and tri-alkyl siloxy substituents. As used herein the term "lower alkyl" refers to alkyl groups comprised of 1 to 4 carbon atoms.

Specific examples of suitable epoxides include those of formula IV:

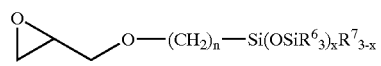

Wherein $R^6$ and $R^7$ are independently selected from alkyl groups having 1 to 4 carbon atoms, n is an integer between 1 and 12 and x is an integer between 0 and 3. Even more specifically, the epoxide may be (3-glycidoxypropyl)bis (trimethylsiloxy)methylsilane.

Epoxides may be formed in a number of ways including, but not limited to, oxidation of alkenes with peroxyacids, formation by an intramolecular $SN^2$ reaction in which there is a trans halohydrin moiety, addition of a nucleophilic oxidizing agent (such as a basic solution of hydrogen peroxide) to an $\alpha,\beta$-unsaturated carbonyl compound, and the reaction of a, sulfonium ylide with a carbonyl compound. Alternatively, epoxides substituted with a Si containing group may be prepared by the hydrosilylation of an already formed epoxide containing an allyl functionality. Such methods are well known to those skilled in the art and this list of synthetic routes to epoxides and epoxides substituted with a Si containing group, in no way limits the scope of this invention to these preparations.

According to the process of the present invention the epoxide is reacted with at least one acrylic acid and at least one epoxide opening catalyst. Suitable acrylic acids comprise between 1 and 4 carbon atoms. Preferably said acid is methacrylic acid. The reaction between the epoxide and the acrylic acid may be equimolar, however, it may be advantageously performed with an excess of acrylic acid. Accordingly, the acrylic acid may be used in amounts between about 1 and about 3 moles of acrylic acid per mole epoxide.

The epoxide opening catalyst used in the first step of the present invention may be any catalyst which is known in the art to open the epoxide ring. Suitable epoxide opening catalysts include Lewis acids, Lewis bases, Bronsted acids and porphyrin complexes, combinations thereof and the like. A preferred class of epoxide opening catalysts include alkali metal salts of acrylic acids. Suitable alkali metals include Li and K and Na and suitable acrylic acids comprise between one and four carbon atoms. Preferably said alkali metal salt is the Li or K salt of methacrylic acid. The epoxide opening catalyst is added in an amount sufficient to catalyze the reaction, and preferably in an amount up to about 0.5 equivalents, based upon the epoxide.

An inhibitor may also be included with the reactants. Any inhibitor which is capable of reducing the rate of polymerization may be used. Suitable inhibitors include hydroquinone monomethyl ether, butylated hydroxytoluene, mixtures thereof and the like. The inhibitor may be added in an amount up to about 10,000 ppm, and preferably in an amount between about 1 and about 1,000 ppm.

The first reaction is conducted for a time and temperature sufficient to provide a percent conversion of substituted epoxide between about 50 and 85% and preferably between about 70 and 85%. Suitable temperatures include elevated temperatures, preferably greater than about 60° C. and more preferably between about 80° C. and about 110° C. Suitable reaction times include up to about 8 hours, preferably up to about six hours and more preferably between about 2 and about 6 hours. It will be appreciated by those of skill in the art the temperature and reaction time are inversely proportional, and that higher reaction temperatures may allow for decreased reaction times and vice versa Also, other reaction conditions which slow down the rate of reaction, such as decreased catalyst concentration, may also be used in the process of the present invention.

The product mixture from the first reaction step (the "first reaction product") is reacted with a nucleophilic compound which selectively reacts with any remaining substituted epoxide. Also, suitable nucleophiles should be readily removed from the second reaction product upon treatment with the selected purification step. Suitable nucleophilic compounds include primary, secondary, and tertiary amine containing compounds, and preferably primary and secondary amines. Specific examples of nucleophilic compounds include isopropylamine, diisopropylamine, phthalimide, and mixtures thereof. The nucleophilic compound is used in amounts which are about equimolar with any unreacted epoxide remaining after the first reaction step.

The second reaction step may be conducted at a temperature which is less than the boiling point of the selected nucleophilic compound, and is readily conducted at ambient temperature or elevated temperatures. Suitable temperatures include those between about 25° C. and about 90° C. Reaction pressure for the second reaction step is not critical, and ambient pressure may be used. It will be appreciated by those of skill in the art the pressure and reaction time are inversely proportional, and that higher reaction pressuress may allow for decreased reaction times and vice versa. The second reaction step is preferably conducted for a time sufficient to convert substantially all epoxide to the nucleophile derivative of said substituted epoxide. Suitable second reaction times include those up to about 16 hours, and preferably between about 4 and 16 hours.

The product of the second reaction step may be purified to remove the nucleophile derivative by various methods including acidic extraction, treatment with ionic exchange resins, ionic exchange columns, combinations thereof and the like. Conventional conditions for these purification methods are known in the art.

It has been found that by conducting the reaction for reaction times shorter than those previously used, and treating the first reaction mixture with a nucleophilic compound SiAGMA compounds having improved purity with respect to the difunctional byproducts may be produced. Specifically, the SiAGMA compounds produced by the process of the present invention have difunctional components, which act as crosslinkers in amounts less than about 5 weight % dimethacrylates.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

The following abbreviations are used in the examples below:

SiMAA2 bis(trimethylsilyloxy)methylsilylpropylglycerol methacrylate (CA Index name is 2-propenoic acid, 2-methyl, 2-hydroxy-3-[3-[1,3,3,3-tetramethyl-1-[(trimethylsilyl)oxy]disiloxanyl]propoxy]propyl ester)

MEHQ hydroquinone monomethyl ether

Epoxide (3-glycidoxypropyl)bis(trimethylsiloxy)methylsilane

Percent conversion was determined using GC as follows. A 100 uL sample was dispersed into 1 mL IPA. The dispersed samples were analyzed using a GC-FID and conditions listed below:

Carrier Gas: Helium
Carrier Gas Pressure: 70 PSI
Total Flow: 75 mL/min
Septum purge: 3–5 mL/min
Hydrogen Pressure: 60 PSI
Air Pressure: 30 PSI
Detector: Flame ionization detector @ 280° C.
Inlet temperature: 280° C.
Autosampler wash solvent: isopropyl alcohol
Column: Restek RTX-5 30 m×0.25 mm×1.0 um (5% diphenyl, 95% dimethyl polysiloxane)
Injection Volume: 2 ul (100:1) split
Temperature Program:
  Initial Temperature: 60° C.
  Ramp: 10° C./min
  Final Temp: 325° C.
  Final time: 5 min
  Equilibrate: 7 min

EXAMPLE 1

To a three-neck, 250 mL round bottom reaction flask equipped with a magnetic stir bar, drying tube, and a thermocouple, was added 0.60 g potassium methacrylate (4.8 mmol, 0.08 equivalents) and 10.36 grams methacrylic acid (0.12 mol, 2 equivalents). MEHQ (45 mg, 0.36 mmol, 0.006 equivalents) was added to the reaction flask. The reaction was stirred. With stirring, was added 20.0 grams of Epoxide (obtained from Silar, 0.060 mol). The mixture was heated to 100° C.

After five and a half hours, a small aliquot (≈200 mL) of the reaction mixture was removed, diluted with hexanes (≈1 mL) and washed successively with ≈mL 0.5 M aqueous NaOH and ≈1 mL 2.5 weight % aqueous NaCl. The organic layer was analyzed by GC and shown to contain 24.5% of starting Epoxide and 75.5% SiMAA2. No other products were observed by GC.

The reaction mixture was then removed from heat and transferred to a separatory funnel using ≈100 mL hexanes for transfer and to dilute the mixture. The hexanes layer was washed successively with 2x≈75 mL 0.5 M aqueous NaOH and ≈75 mL 2.5 weight % aqueous NaCl. The organic layer was then dried over $Na_2SO_4$ and filtered. The filtrate was concentrated on the rotary evaporator at 55° C. This concentrate, as analyzed by GC, was shown to contain 25% staring Epoxide and ≈74% SiMAA2.

To the solution of Epoxide and SiMAA2 was added 6.60 mLs isopropylamine (0.076 mol, 5.1 equivalents). The reaction mixture was stirred at 40° C. overnight using a magnetic stir bar. An aliquot was removed from the reaction solution and analyzed by GC. GC results confirmed that the reaction solution contained no starting Epoxide. The magnetic stir bar was removed from the reaction vessel and the solution concentrated on the rotovap to remove excess isopropylamine (bp 33–34° C.). The concentrated solution was removed from the rotovap and diluted with ≈50 mL methanol. To this was added, Amberlite®IR120 (plus) resin was added until the mixture was pH ≈7. The mixture was left stirring, using a magnetic stir bar, for one hour. After one hour, the mixture was filtered and the filtrate concentrated on the rotovap to give SiMAA2. The resulting SiMAA2 was analyzed by LC-MS for purity. Purity results are listed below in Table 1 and are compared to SiMAA2 purities made using other reaction conditions which are described in Examples 2 and 3.

EXAMPLE 2

To a three-neck, 5000 mL round bottom reaction flask equipped with a magnetic stir bar, drying tube, and a thermocouple, was added 92 g dry lithium methacrylate (1 mol, 0.17 equivalents) and 1023 grams methacrylic acid (11.91 mol, 2 equivalents). MEHQ (4.65 g, 0.037 mol, 0.006 equivalents) was added to the reaction flask. The reaction was stirred. With stirring, was added 2000 grams of Epoxide (obtained from Silar, 5.95 mol). The reaction mixture was heated to 90° C.

After about fifteen hours, the reaction mixture was removed from heat, allowed to cool to about 50° C. and transferred to a separatory funnel using ≈3200 mL hexanes for transfer and to dilute the mixture. The hexanes layer was washed successively with 4x≈-3200 mL and 1x2000 mL 0.5 M aqueous NaOH, and ≈75 mL 2.5 weight % aqueous NaCl. The organic layer was then dried over $Na_2SO_4$ and filtered.

To the filtrate was added 800 g of flash grade silica gel. The inhomogeneous mixture was agitated for three hours at room temperature and filtered over a fritted glass funnel. The filtrate was then concentrated on the rotary evaporator, at 55° C., to give SiMAA2. The resulting SiMAA2 was analyzed by LC-MS for purity. Purity results are listed in Table 1, below.

EXAMPLE 3

To a three-neck, 5000 mL round bottom reaction flask equipped with a magnetic stir bar, drying tube, and a thermocouple, was added 59 g dry potassium methacrylate (0.476 mol. 0.08 equivalents) and 1023 grams methacrylic acid (11.91 mol, 2 equivalents). MEHQ (4.65 g, 0.037 mol, 0.006 equivalents) was added to the reaction flask. The reaction was stirred. With stirring, was added 2000 grams of Epoxide (obtained from Silar, 5.95 mol). The reaction mixture was heated to 100° C.

After about fifteen hours, the reaction mixture was removed from heat, allowed to cool to room temperature and transferred to a separatory funnel using ≈2000 mL hexanes for transfer and to dilute the mixture. The hexanes layer was washed successively with 3x≈:5000 mL 0.5 M aqueous NaOH, and 3 x=3500 mL 2.5 weight % aqueous NaCl. The organic layer was then dried over $Na_2SO_4$ and filtered. The filtrate was then concentrated on the rotary evaporator, at 55° C., to give SiMAA2. The resulting SiMAA2 was analyzed by LC-MS for purity. Purity results are listed in Table 1, below.

TABLE 1

| | Wt % Component | | |
|---|---|---|---|
| Component | Example 1 | Example 2 | Example 3 |
| Total Purity (%) | 78.9 | 85.9 | 84 |
| Difunctional impurities (%) | 1.82 | 4.92 | 8.97 |
| Ethyl Acetate (%) | <0.05 | <0.02 | 0.43 |
| Hexanes (%) | 0.35 | <0.06 | <0.6 |
| Epoxide (%) | 1.34 | 0.59 | <0.06 |
| Glycol (%) | 9.96 | 0.49 | 0.76 |

We claim:

1. A process comprising the steps of
   (a) reacting a first reaction mixture comprising substituted epoxide with at least one epoxide opening catalyst and at least one acrylic acid to form a first reaction product wherein between about 50 and about 85% of the substituted epoxide is converted to glycerol acrylate;
   (b) treating said first reaction mixture with a nucleophilic compound to form a second reaction product which is substantially free of said substituted epoxide and which comprises said substituted glycerol acrylate and a nucleophile derivative of said substituted epoxide; and
   (c) treating said second reaction product to remove said nucleophile derivative and produce substituted glycerol acrylate having less than about 5 weight % difunctional impurities.

2. The process of claim 1 wherein said substituted epoxide comprises at least one compound of Formula II

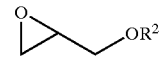

wherein $R^2$ is selected from the group consisting of C1 to C12 alkyls substituted with at least one Si containing moiety.

3. The process of claim 2 wherein $R^2$ is selected from the group consisting of C1 to C6 alkyls substituted with at least one siloxane.

4. The process of claim 1 wherein said substituted epoxide comprises at least one compound of formula III:

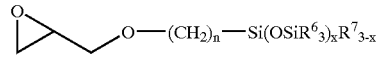

wherein $R^6$ and $R^7$ are independently selected from alkyl groups having 1 to 4 carbons, n is an integer between 1 and 12 and x is an integer between 0 and 3.

5. The process of claim 2 wherein said Si containing moiety has the formula III:

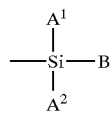

wherein $A^1$ and $A^2$ are the same or different and are selected from lower alkyl and B is a group of the structure:

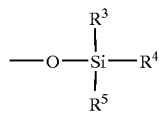

wherein $R^3$, $R^4$ and $R^5$ are the same or different and are selected from the group including lower alkyl, phenyl, benzyl, and tri-alkyl siloxy substituents.

6. The process of claim 1 wherein said substituted epoxide comprises (3-glycidoxypropyl)bis(trimethylsiloxy) methylsilane.

7. The process of claim 1 wherein said acrylic acid comprises methacrylic acid.

8. The process of claim 1 said acrylic acid is used in amounts between about 1 and about 3 moles of acrylic acid per mole substituted epoxide.

9. The process of claim 1 wherein said epoxide opening catalyst is selected from the group consisting of Lewis acids, Lewis bases, Bronsted acids and porphyrin complexes.

10. The process of claim 1 wherein said epoxide opening catalyst comprises an alkali metal salt.

11. The process of claim 10 wherein said alkali metal salt comprises at least one alkali metal selected from the group consisting of Li, K and Na.

12. The process of claim 10 wherein said at least one alkaline earth acrylic acid salt comprises between one and four carbon atoms and said at least one acrylic acid comprises between one and four carbon atoms.

13. The process of claim 10 wherein said alkali metal salt is a Li or K salt of methacrylic acid.

14. The process of claim 1 wherein said alkali metal salt is present in an amount up to about 0.5 equivalents, based upon the epoxide.

15. The process of claim 1 whereat said first reaction mixture further comprises at least one inhibitor.

16. The process of claim 15 wherein said inhibitor is selected from the group consisting of hydroquinone monomethyl ether, butylated hydroxytoluene and mixtures thereof.

17. The process of claim 15 wherein said inhibitor is added in an amount up to about 10,000 ppm.

18. The process of claim 15 wherein said inhibitor is added in an amount between about 1 and about 1,000 ppm.

19. The process of claim 1 wherein step (a) reaction conditions comprise a temperature between about 80° C. and about 110° C. and a reaction time between about 2 and about 6 hours.

20. The process of claim 1 wherein said nucleophilic compound is selected from the group consisting of primary, secondary, and tertiary amine containing compounds, and mixtures thereof.

21. The process of claim 20 wherein said nucleophilic compounds are selected from the group consisting of isopropylamine, diisopropylamine, phthalimide, and mixtures thereof.

22. The process of claim 1 wherein step (c) comprises acidic extraction, treatment with ionic exchange resins, ionic exchange columns and combinations thereof.

23. The process of claim 1 wherein said first reaction product comprises between about 60% and about 80% substituted glycerol acrylate.

24. A process comprising the steps of
 (a) reacting a first reaction mixture comprising substituted epoxide with at least one alkali metal salt and at least one acrylic acid at a temperature greater than about 60° C. and for up to about 6 hours to form a first reaction wherein between about 50 and about 85% of the substituted epoxide is converted to glycerol acrylate;
 (b) treating said first reaction mixture with a nucleophilic compound at a temperature between about 20° C. and 90° C. for up to about 16 hours to form a second reaction product which is substantially free of said substituted epoxide and which comprises said substituted glycerol acrylate and a nucleophile derivative of said substituted epoxide; and
 (c) treating said second reaction product to remove said nucleophile derivative and produce substituted glycerol acrylate having less than about 5 weight % difunctional impurities.

* * * * *